United States Patent [19]

Krasznai et al.

[11] 4,164,656

[45] Aug. 14, 1979

[54] PARALLEL SAFETY COUPLING FOR X-RAY TABLE TILT DRIVE

[75] Inventors: Charles Z. Krasznai, Trumbull; Donald J. Meshkil, Milford; Morris Krumholtz, Bridgeport, all of Conn.

[73] Assignee: U.S. Philips Corporation, New York, N.Y.

[21] Appl. No.: 798,992

[22] Filed: May 20, 1977

[51] Int. Cl.² .................... G01N 21/00; G01N 23/00; G21K 5/06; G21K 5/08
[52] U.S. Cl. ................................ 250/439 R; 250/456; 269/322; 269/323
[58] Field of Search ............... 250/439, 446, 448, 456, 250/523; 269/322, 323; 108/6, 7, 8; 74/520; 188/129

[56] References Cited

U.S. PATENT DOCUMENTS

| | | | |
|---|---|---|---|
| 3,588,500 | 6/1971 | Koerner | 250/439 |
| 3,902,070 | 8/1975 | Amor | 250/523 |

*Primary Examiner*—Alfred E. Smith
*Assistant Examiner*—Thomas P. O'Hare
*Attorney, Agent, or Firm*—Thomas A. Briody; Edward J. Connors, Jr.; Jack E. Haken

[57] ABSTRACT

A safety coupling for an X-ray table tilt drive. An auxiliary coupling means in parallel with the main mechanical drive coupling has a substantially constant amount of free play over the entire operational tilt range of the table so that it ordinarily carries none of the drive force. In the event of mechanical failure of the main drive coupling the free play is taken up and the auxiliary coupling prevents the table from abruptly falling to the rest position.

11 Claims, 6 Drawing Figures

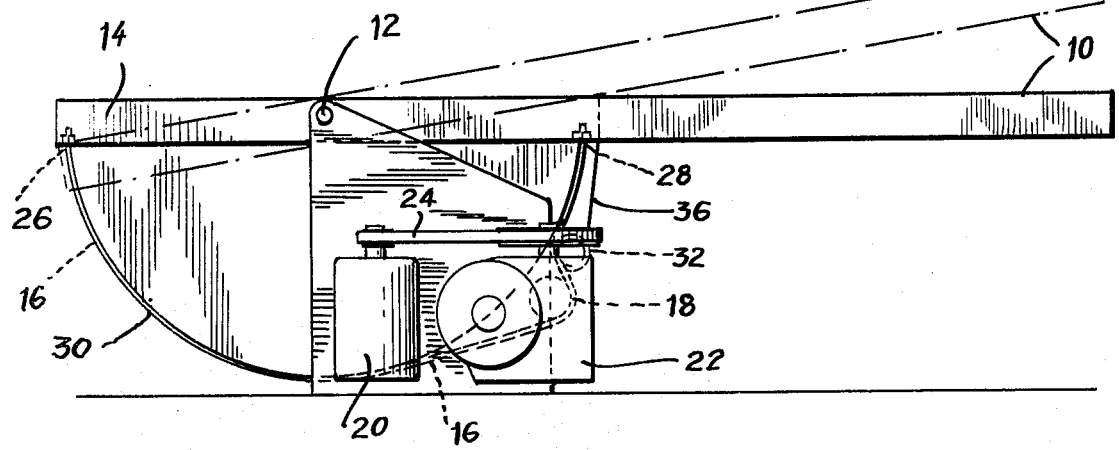
Fig. 1.
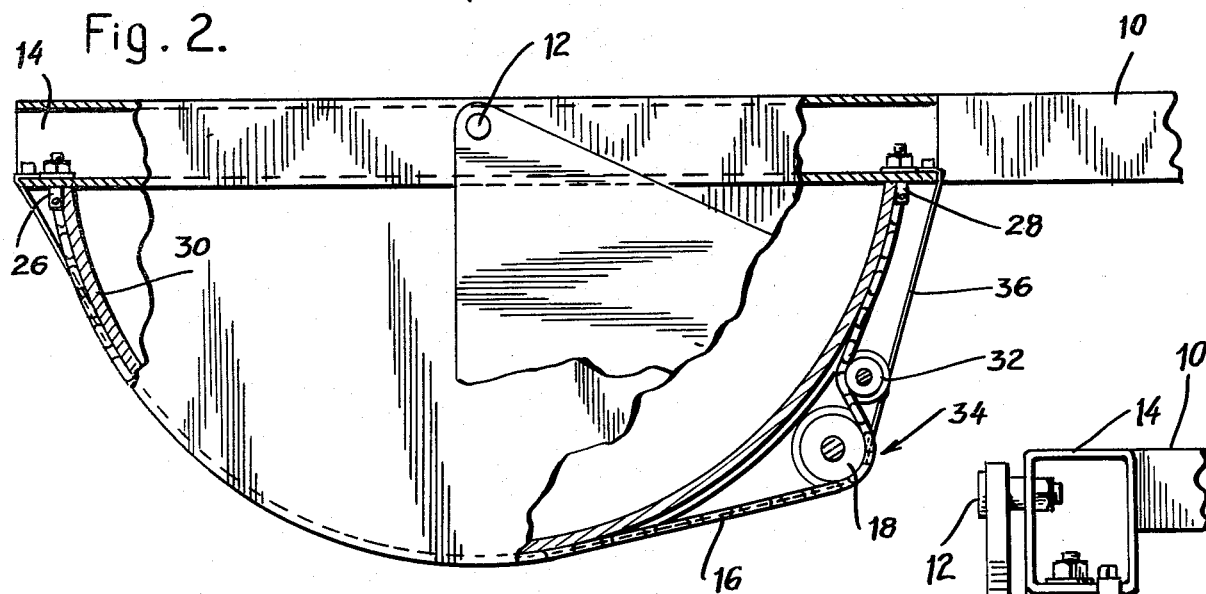
Fig. 2.
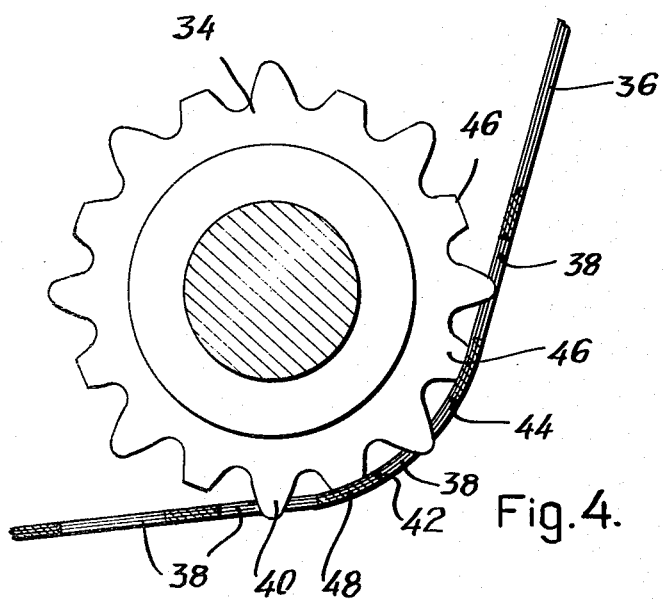
Fig. 3.
Fig. 4.

PARALLEL SAFETY COUPLING FOR X-RAY TABLE TILT DRIVE

BACKGROUND OF THE INVENTION

This invention relates to medical X-ray tables and more specifically to tilt drives and safety restraint apparatus therefor.

For general X-ray diagnostic use as well as for many specialized uses it is very desirable if not necessary to move a patient resting upon an X-ray table into different orientations. One of the more common and useful movements is a tilting movement, where the patient is brought from standing position to prone position or vice versa. A convenient height for the table results in a rotation axis that is not at the center of the table, which causes a weight unbalance. The weight unbalance tends to make the table abruptly fall to a rest position in the event of mechanical failure of the tilt drive therefor. An abrupt fall of the table can easily injure an attendant or the patient supported on the table.

One solution is to better balance the table either by effectively moving the rotation axis closer to center or by using a counterweight for the table. A more practical solution is to prevent the table from falling abruptly with some kind of safety apparatus. Shock absorbers have been used for this purpose. Shock absorbers do not prevent a falling of the table, but rather safely limit the rate of fall. Another approach has been to design the table tilt drive so that mechanical failure will not occur due to the high mechanical reliability of the tilt drive. Heavy gear trains and rack and pinion arrangements have been used for this purpose.

It is an object of the present invention to prevent an abrupt fall of the X-ray table in the event of mechanical failure of the table tilt drive.

A further object is to prevent any substantial falling of the X-ray table at all in the event of mechanical failure of the table tilt drive.

Another object is to provide a safety restraint apparatus which safely allows use of tilt drive constructions which are susceptible to possible mechanical failure.

Still another object is to provide a less expensive tilt drive which is nevertheless safe to use.

A further object is to provide safety apparatus for a table tilt drive which allows continued temporary use of the table even after mechanical coupling failure in the tilt drive.

SUMMARY OF THE INVENTION

An auxiliary coupling means in parallel with the main mechanical drive coupling has a substantially constant amount of free play over the entire operational tilt range of the table so that it ordinarily carries none of the drive force. In the event of mechanical failure of the main drive coupling the free play is taken up and the auxiliary coupling prevents the table from abruptly falling to the rest position. The auxiliary coupling may also temporarily function in place of the main drive coupling for temporary operation of the tilt drive. In the preferred embodiment the main drive coupling is a sprocket wheel and roller chain arrangement. The parallel auxiliary coupling means may comprise a parallel sprocket wheel and inexpensive band having slots for receiving the sprocket teeth. The sprocket band and roller chain are at the same pitch diameter and free play is created by oversizing the slots in the sprocket band. Another auxiliary coupling means is a safety wire and wire take-up drum, the take-up drum and roller chain sprocket wheel providing the same effective pitch diameter. Free play is created by giving the wire a small amount of slack.

The invention will now be described more fully by reference to the accompanying drawings.

BRIEF DESCRIPTION OF THE DRAWINGS

FIG. 1 is a side view of an X-ray table and tilt drive therefor.

FIG. 2 shows the main mechanical drive coupling in more detail and a first embodiment of the auxiliary coupling means.

FIG. 3 is an end view of the embodiment of FIG. 2.

FIG. 4 shows in more detail the first embodiment of the auxiliary coupling means.

DETAILED DESCRIPTION OF THE PREFERRED EMBODIMENTS

Figure 5:
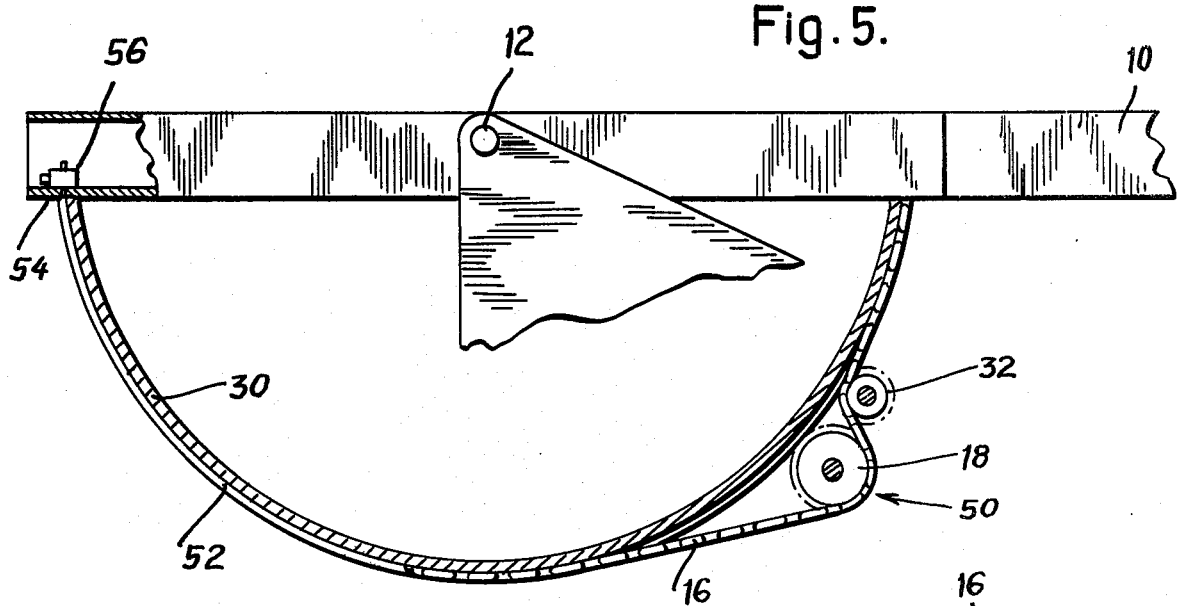
FIG. 5 shows the main drive coupling with a second embodiment of the auxiliary coupling means.

Referring now to FIGS. 1 and 2, a patient supporting X-ray table 10 is axially mounted for tilting movement about an axis of rotation 12. Two possible orientations for the table 10 are shown. The rest position for table 10 is indicated in solid lines and a tilted position is shown in broken lines. Tilting from the rest position is achieved by downward force applied to the left end 14 of the table via a roller sprocket chain 16 attached thereto. Roller chain 16 is pulled downward by drive sprocket wheel 18 which is powered by drive motor 20 via a gear reduction 22 and belt coupling 24. The ends of roller chain 16 are attached to the table 10 via nut and bolt connectors 26 and 28 (FIG. 2), so that fine adjustment of chain length and tension can be made by tightening or loosening the nuts. Roller chain 16 is held in a semicircular configuration coaxial with respect to the axis of rotation 12 by a guide channel 30. Idler sprocket 32 cooperates with sprocket 18 to assure engagement between the sprocket teeth of sprocket 18 and the links of the roller chain 16. Idler sprocket 32 may also act to hold tension on the roller chain 16. However, substantially no change in slack or tension of roller chain 16 occurs over the full operational range of the tilt drive because of the semicircular configuration of the roller chain is coaxial with the axis of rotation of the table.

In parallel with the main mechanical drive coupling means, comprising chain 16 and sprocket 18, is an axuiliary coupling means comprising an auxiliary sprocket wheel 34 coaxially attached to the drive sprocket wheel 18 for common rotation therewith and a sprocket band 36 operatively associated with the auxiliary sprocket wheel 34. The auxiliary sprocket wheel 34 may be identical to the sprocket 18 except that alternate sprocket teeth are cut down as shown in FIG. 4. Band 36 has oversized sprocket slots 38 so that the full sprocket teeth 40 do not ordinarily engage edges 42, 44 of the slots 38. The oversized slots 38 provide free play between the band 36 and auxiliary sprocket wheel 34 so that band 36 ordinarily carries no part of the drive force transferred from the motor 20 to the table 10. The free play provided by oversized slots 38 remains constant because the size of the slots is constant and because the full teeth 40 ordinarily remian substantially in the center of the slots 38 as shown in FIG. 4. Upon mechanical failure of chain 16, table 10 drops just enough to take up the free play and bring teeth 40 into engagement with edges 44 of slots 38, at which point band 36 takes up the drive load and functions at least temporarily in place of the chain. Preferably the axis of rotation of the table is midway between an end of the table and the center of gravity of the table and substantially parallel with the plane of the table and eccentrically displaced from but substantially parallel to the transverse axis thereof so that the table can be rotated to bring a patient thereon from a prone position to a standing position or vice versa.

In order to assure that the full teeth 40 do remain in the center of the slots 38, the effective pitch diameter of the sprockets 18 and 34 must be substantially identical. In other words when sprockets 18 and 34 make one full revolution, band 36 must be advanced by sprocket 34 by substantially the same amount as chain 16 is advanced by sprocket 18. Cutoff teeth 46 of sprocket 34 engage the band 36 at regions 48 between the slots to hold the band 36 out at a predetermined effective diameter which is substantially the same as the effective pitch diameter experienced by chain 16. Thus, the precise amount cut off from teeth 46 determines the effective pitch diameter of the auxiliary coupling, which must be matched to the pitch diameter of the main coupling. The spacing of slots 38 along the band 36 is also dependent upon the pitch diameter determined by the cut-off teeth 46.

As will be apparent, slots 38 must be spaced so that teeth 40 remain substantially centered within the slots. The most straightforward way to achieve this is to match effective pitch diameters and then uniformly space slots 38 in accordance with the effective pitch diameter and spacing of teeth 40 about sprocket 34. It is possible to use non-uniformly spaced slots and teeth and theoretically at least also different pitch diameters. but the mechanical arrangement and construction is complicated thereby. The two sprockets 18, 34 may be of separate construction and bolted or otherwise attached together, or they may be of unitary construction with a single wheel having more than one set of sprockets. Chain 16 may be a double roller chain as shown in FIG. 3 cooperating with a double sprocket or it may be a single sprocket roller chain. Other variations will be immediately apparent to one skilled in the mechanical arts.

Figure 6:
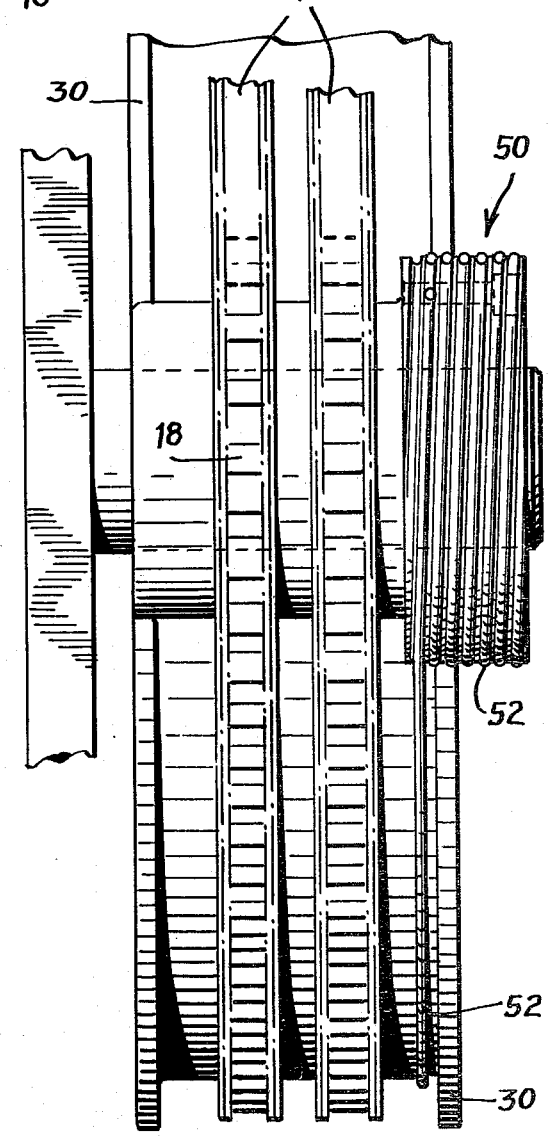
FIG. 6 is an end view of the embodiment of FIG. 5.

Another embodiment for the auxiliary coupling is shown in FIGS. 5 and 6. In place of the auxiliary sprocket wheel is a drum 50 having a helical groove to receive a wire or rope 52 would thereon. The other end of wire 52 is attached to table 10 at point 54. The helical groove assures that the wire winds onto the drum at a constant and predetermined effective pitch diameter, which here again must be matched to the effective pitch diameter of the sprocket 18 and chain 16 combination. Free play is provided by allowing a slight slack in the wire 52, so that the wire does not ordinarily carry any of the drive load. Upon failure of chain 16, table 10 drops just sufficiently to take up the slack, at which point wire 52 acts in place of chain 16 to take up the load and prevent the table from falling abruptly to the rest position.

In this embodiment the table must tend to always fall in the same direction because the wire cannot take up a load in both directions. It is obviously possible to add a second wire to take up the load in the other direction but table tilt drives do not ordinarily tilt the table past vertical, so that a safety restraint against falling in the opposite direction is not ordinarily needed.

In both embodiments the auxiliary coupling band or wire is positioned inside of the same guide channel 30 with the chain 16. It is possible to provide separate guide channels for the main coupling and the auxiliary safety coupling but this is not ordinarily required. Separate guides may be required if the effective semicircular channel length for the two flexible couplings is not sufficiently matched with a single channel or if a difference in effective pitch diameters demands a difference in length for the flexible couplings.

What is claimed is:

1. X-ray apparatus, comprising:
a patient supporting table axially mounted for tilting movement about an axis of rotation, said axis of rotation being eccentric to said table such that gravity tends to return said table to a rest position;
a drive motor;
a main mechanical drive coupling means linking said motor to said table for tilting said table about said axis of rotation as said motor rotates;
an auxiliary coupling means between said motor and said table in parallel with said main coupling means for preventing an abrupt falling of said table to the rest position upon a mechanical failure of said main mechanical drive coupling means, said auxiliary coupling means having a substantially constant amount of mechanical free play over the entire operational tilt range of said table, said free play being sufficient to assure that said auxiliary coupling means carries no part of the drive force transferred from said motor to said table except in the event of mechanical failure of said main coupling means, in which event said auxiliary coupling means links said motor to said table after take up of said free play, said substantially constant free play being sufficiently small to prevent an unsafe amount of table drop during take up of said free play.

2. X-ray apparatus as defined in claim 1, wherein said table is mounted for rotation about an axis such that a patient supported by said table is substantially in prone position when said table is at rest position and substantially in standing position when said table is at full tilt.

3. X-ray apparatus as defined in claim 1, wherein said axis of rotation of said table is substantially parallel with the plane of the table and eccentrically displaced from but substantially parallel to the transverse axis thereof.

4. X-ray apparatus as defined in claim 3, wherein said axis of rotation is positioned approximately midway between an end of said table and the center of gravity thereof.

5. X-ray apparatus as defined in claim 1, wherein said main mechanical drive coupling means comprises a drive sprocket wheel mechanically coupled to said drive motor for common rotation therewith and a sprocket chain in operative engagement with said drive sprocket wheel and attached to said table such that said table rotates about said axis as said drive sprocket wheel rotates.

6. X-ray apparatus as defined in claim 5, wherein said auxiliary coupling means comprises an auxiliary sprocket wheel coaxially attached to said drive sprocket wheel for common rotation therewith and a sprocket band operatively associated with said auxiliary sprocket wheel and attached to said table in parallel with said sprocket chain, said drive and auxiliary sprocket wheels having substantially the same effective pitch diameter and said sprocket band having oversized sprocket slots therein to provide said free play.

7. X-ray apparatus as defined in claim 6, wherein said drive and auxiliary sprocket wheels are constructed as a single wheel having two separate parallel sets of sprocket teeth.

8. X-ray apparatus as defined in claim 6, and further comprising a guide channel means for holding said sprocket chain and said sprocket band in approximate semicircular configuration with respect to said axis of rotation of said table.

9. X-ray apparatus as defined in claim 5, wherein said auxiliary coupling means comprises a drum coaxially attached to said drive sprocket wheel for common rotation therewith and a wire attached at one end to said drum for winding about said drum and attached at the other end to said table in parallel with the portion of said sprocket chain which is under tension load when said table is not at rest position, said drum and drive sprocket wheel having substantially the same effective pitch diameter and said wire having slack to provide said free play.

10. X-ray apparatus as defined in claim 9, wherein said drum has a helical groove running about the surface thereof for receiving the wire as it winds onto the drum to prevent the wire from overlapping itself, and changing pitch diameter.

11. X-ray apparatus as defined in claim 9, and further comprising a guide channel means for holding said sprocket chain and the portion of said wire not wound on said drum in approximate semicircular configuration with respect to said axis of rotation of said table.

* * * * *

UNITED STATES PATENT AND TRADEMARK OFFICE
CERTIFICATE OF CORRECTION

PATENT NO. : 4,164,656
DATED : August 14, 1979
INVENTOR(S) : CHARLES Z. KRASZNAI ET AL It is certified that error appears in the above-identified patent and that said Letters Patent are hereby corrected as shown below:

On the Title Page, Section [75], "Donald J. Meshkil" should be

--Donald J. Mishkel--

Signed and Sealed this

Eleventh Day of March 1980

[SEAL]

Attest:

SIDNEY A. DIAMOND

Attesting Officer

Commissioner of Patents and Trademarks